(12) United States Patent
Thuerk

(10) Patent No.: US 7,756,726 B2
(45) Date of Patent: Jul. 13, 2010

(54) SECURED MEDICAL SIGN-IN

(75) Inventor: Keith A. Thuerk, Southlake, TX (US)

(73) Assignee: International Business Machines Corporation, Armonk, NY (US)

( * ) Notice: Subject to any disclaimer, the term of this patent is extended or adjusted under 35 U.S.C. 154(b) by 1748 days.

(21) Appl. No.: 10/670,678

(22) Filed: Sep. 25, 2003

(65) Prior Publication Data
US 2005/0071188 A1 Mar. 31, 2005

(51) Int. Cl.
G06Q 10/00 (2006.01)
G06Q 50/00 (2006.01)

(52) U.S. Cl. .......................................................... 705/2
(58) Field of Classification Search ...................... 705/2, 705/3, 4, 1; 345/342; 359/40; 709/206; 725/35
See application file for complete search history.

(56) References Cited

U.S. PATENT DOCUMENTS

| 5,526,146 | A | * | 6/1996 | Goodman et al. ............... 349/5 |
| 5,564,068 | A | | 10/1996 | Nguyen |
| 5,614,703 | A | | 3/1997 | Martin et al. |
| 5,664,109 | A | * | 9/1997 | Johnson et al. ................. 705/2 |
| 5,801,697 | A | * | 9/1998 | Parikh et al. ................. 715/790 |
| 5,855,550 | A | | 1/1999 | Lai et al. |
| 5,897,493 | A | * | 4/1999 | Brown ......................... 600/300 |
| 5,911,687 | A | | 6/1999 | Sato et al. |
| 5,987,421 | A | | 11/1999 | Chuang |
| 6,112,986 | A | | 9/2000 | Berger et al. |
| 6,161,316 | A | | 12/2000 | Bolon |
| 6,314,165 | B1 | | 11/2001 | Junqua et al. |
| 6,314,405 | B1 | | 11/2001 | Richardson |
| 6,322,502 | B1 | | 11/2001 | Schoenberg et al. |
| 6,394,356 | B1 | | 5/2002 | Zagami |
| 6,401,138 | B1 | | 6/2002 | Judge et al. |
| 2002/0022973 | A1 | * | 2/2002 | Sun et al. ......................... 705/3 |
| 2002/0059587 | A1 | * | 5/2002 | Cofano et al. .................. 725/35 |
| 2002/0065668 | A1 | * | 5/2002 | Goodwin et al. ................ 705/1 |
| 2003/0229670 | A1 | * | 12/2003 | Beyda ........................ 709/206 |

OTHER PUBLICATIONS

"Transaction Completion Code Based on Digital Signatures", IBM Technical Disclosure Bulletin, vol. 28, No. 3, pp. 1109-1122, Aug. 1985.

* cited by examiner

Primary Examiner—Gerald J. O'Connor
Assistant Examiner—John A Pauls
(74) Attorney, Agent, or Firm—Novak Druce + Quigg

(57) ABSTRACT

A method for concealing displayed confidential information includes providing one or more publically accessible displays and one or more private displays, receiving confidential information, displaying at least a portion of the confidential information at the private display, and displaying at least a portion of the confidential information at the publically accessible display for an amount of time determined by an occurrence of an event where the event includes at least one of an expiration of a time period and a user request. The method can also include sending a notification signal where the notification signal can be sent to a health care professional and storing at least a portion of the confidential information. The method can also include concealing at least a portion of the confidential information at the publically accessible display where the concealing step is responsive to a user request.

4 Claims, 2 Drawing Sheets

SECURED MEDICAL SIGN-IN

BACKGROUND OF THE INVENTION

1. Technical Field

This invention relates to the field of privacy protection and, more particularly, to a system for protecting an individual's health information.

2. Description of the Related Art

The ability to provide the appropriate health care to an individual can depend on the health care provider having access to information regarding the patient, particularly including the patient's medical history. Recent advances in digital technologies have enabled health care systems and providers to store vast amounts of information regarding the patient's medical history. This information, in most cases, can be accessed almost instantaneously by health care providers. Additionally, communication networks can enable confidential information to be updated in a central location so that updated information can be accessed from a multitude of remote locations. Thus, the digital revolution and the advances in communication technology have laid the foundation for an infrastructure that gives health care providers access to updated confidential information.

While access to such information can greatly enhance the quality of health care provided to a patient, the amount of personal and confidential information available has caused concern regarding the confidentiality of the patient's private medical information. In reaction to a public outcry for the protection of health care information, the Health Insurance Portability and Accountability Act of 1996 (HIPAA), Public Law 104-191, was enacted on Aug. 21, 1996. Thereafter, the "Privacy Rule" was adopted to elaborate on national standards for safeguards to protect the confidentiality, integrity, and availability of electronically protected health information. The Privacy Rule protects all individually identifiable health information that is held or transmitted by a health care provider. Individually identifiable health information can be information, including demographic data, that relates to the individual's past, present or future physical or mental health or condition, and that identifies the individual or can be used to identify the individual, such as the patient's name, address, birth date, and Social Security Number.

Failure to timely implement these standards to protect such information may, under certain circumstances, trigger the imposition of civil or criminal penalties. For example, civil monetary penalties of $100 per failure can be imposed on entities that fail to comply with a Privacy Rule requirement.

While health care providers need to protect confidential information in order to comply with the Privacy Rule, the logistics of protecting confidential information must balance the protection of confidential information with the need of health care providers to have access to such information. Because many customary health care communications and practices play an important or even essential role in ensuring that individuals receive prompt and effective health care, such a balance must be delicately struck.

Additionally, present health care systems involve a great number of people to provide not only comprehensive health care to a patient, but also to ensure that patients are appropriately billed. Many of these persons do not need to know an individual's private health care information. For example, while a hospital helper may need to know to push the wheelchair of a patient to operating room A so that the patient can have surgery, the hospital helper does not need to know why the patient is having surgery. In stark contrast, it is apparent that a complete medical history should be readily available to the surgeon. Thus, individuals involved in a patient's health care may not need the same amount of access to the patient health care information.

Moreover, due to the nature of the communications and practices of the health care industry, as well as the various environments in which individuals receive health care, the measures incorporated should attempt to eliminate incidental disclosure of confidential information. For example, in a typical emergency room and/or waiting room, one patient may overhear a health care provider's confidential conversation with a patient, or may inadvertently glimpse at an emergency room sign-in sheet that likely contains the patient's name and reason for visiting the emergency room. While such communications may be necessary, health care providers now have a duty to place reasonable safeguards over the unnecessary dissemination of confidential patient information.

SUMMARY OF THE INVENTION

The invention disclosed herein provides a solution for ensuring confidential and private information remains undisclosed to unintended parties when such information is provided in a generally unsecured environment. More particularly, the present invention is a system, method, and apparatus that allows an individual to provide confidential information to a publicly accessible device in which the confidential information is temporarily displayed. Moreover, the system, method, and apparatus allow the appropriate personnel to view the confidential information while preventing unauthorized personnel from accessing the information.

The invention disclosed herein provides a method, system, and apparatus for concealing displayed confidential information. A method for concealing displayed confidential information includes providing one or more publically accessible displays and one or more private displays. The method also includes receiving confidential information, displaying at least a portion of the confidential information at the private display, and displaying at least a portion of the confidential information at the publically accessible display for an amount of time determined by the occurrence of an event. The event includes one or more of an expiration of a time period and a user request. The method can include the step of sending a notification signal where the notification signal can be sent to a health care professional. Additionally, at least a portion of the confidential information can be stored. In another step, at least a portion of the confidential information can be concealed at the publically accessible display, where the concealing is responsive to a user request.

In another embodiment, a method for concealing displayed confidential information includes providing one or more publically accessible displays and one or more private displays. The method also includes receiving confidential information, displaying at least a portion of the confidential information at the publically accessible display, displaying at least a portion of the confidential information at the private display, and concealing at least a portion of confidential information at the publically accessible display. The concealing step can be based on one or more of an expiration of a time period and a user request. The method can also include sending a notification signal, where the notification signal is sent to a health care professional. Further, at least a portion of the confidential information can be stored.

A system for concealing displayed confidential information includes an input system for allowing confidential information to be entered, a first display communicably coupled to the input system for displaying at least a portion of the confidential information to a patient, a second display communicably coupled to the input system for displaying at least a portion of the confidential information. The one or more first displays are configured to conceal at least a portion of the confidential information. The input system can include one or more input devices. Further, the system can include one or more wireless transceivers for sending and/or receiving at least a portion of the confidential information. Additionally, the system can include a housing for supporting the input system and the first display where second display is remotely located from the housing.

BRIEF DESCRIPTION OF THE DRAWINGS

There are shown in the drawings embodiments which are presently preferred, it being understood, however, that the invention is not limited to the precise arrangements and instrumentalities shown.

DETAILED DESCRIPTION OF THE INVENTION

The invention disclosed herein provides a solution for ensuring confidential and private information remains undisclosed to unintended parties when such information is provided in a generally unsecured environment. More particularly, the present invention includes a system, a method, and an apparatus that allow an individual to provide confidential information to a publicly accessible device in which the confidential information is temporarily displayed. Moreover, the present invention allows the appropriate personnel to view the confidential information while preventing unauthorized personnel from accessing the information.

Figure 1:
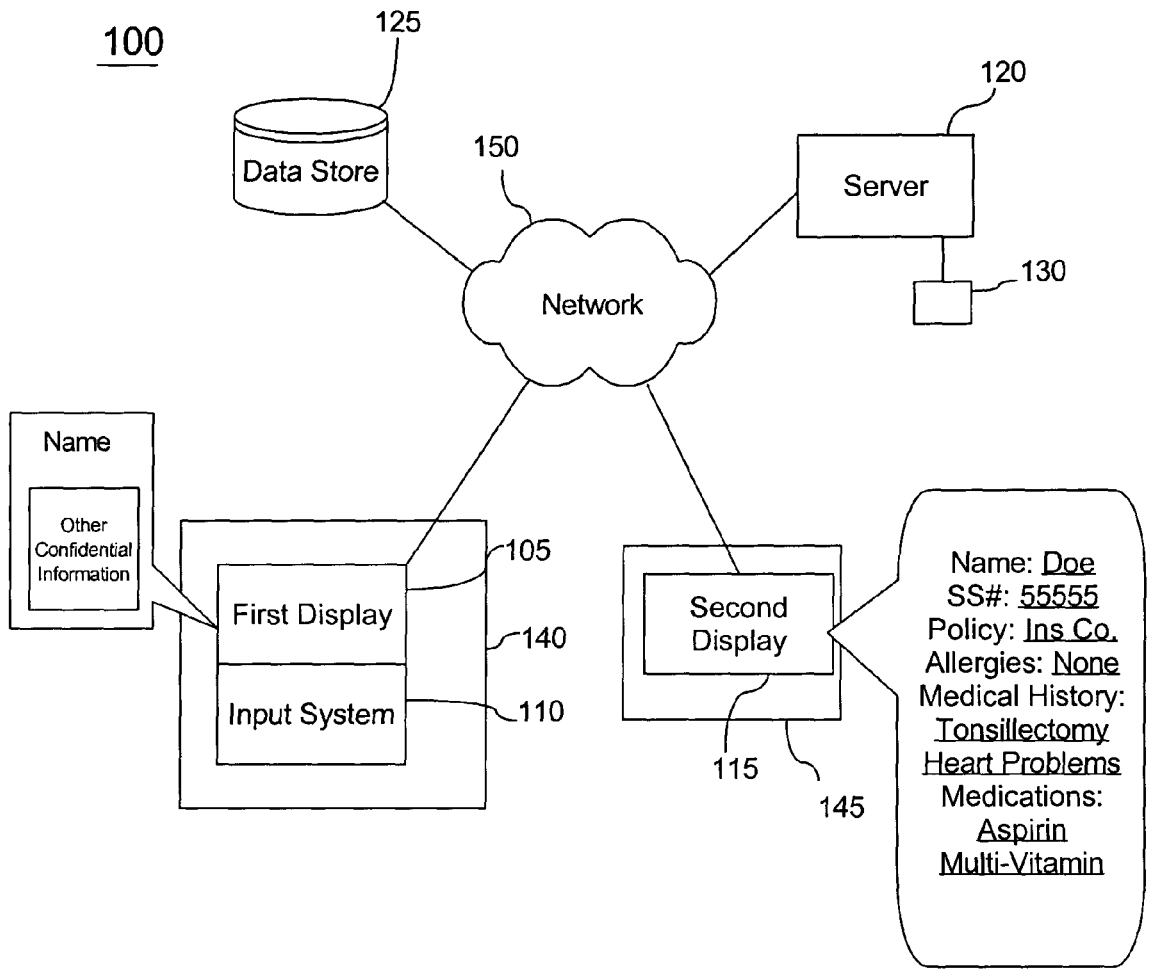
FIG. 1 is a schematic diagram illustrating a system for concealing displayed confidential information in accordance with the inventive arrangements disclosed herein.

FIG. 1 is a schematic diagram illustrating an exemplary system 100 for temporarily displaying confidential information. The system 100 includes a first display 105, an input system 110, a second display 115. The system 100 can also include a server 120, a data store 125, a wireless transceiver 130, and a network 150. Additionally, a housing 140 for the first display 105 and the input system 110, and a housing 145 for the second display, can be included.

The network 150 can communicatively link the various displays, devices, and computing components that form the system 100. The network 150 can utilize any communication medium to facilitate information exchange within the system 100 including, but not limited to, line-based pathways and wireless pathways such as cellular protocols, Wi-Fi, Bluetooth, the 802.11 family of communication protocols, and the like. Moreover, the network 150 can include global networks, local networks, and stand-alone computing devices. For example, the network 150 can include the Internet, intranets, and other sub-networks. Additionally, the network 150 can include mainframes, personal computers, personal data assistants, cellular telephones, land-based telephones, networked peripherals, and other hardware.

The first display 105 is configured to conceal at least a portion of confidential information. The first display 105 can include any device, such as a liquid crystal display, cathode ray tube, plasma screen, and the like, that is suitable for displaying text and/or graphics. Additionally, the first display 105 can be located within a generally unsecured environment that is easily accessible by the public. For example, the first display 105 can be located within the waiting room of a hospital, emergency room, doctor's office, dentist office, and the like. The first display 105 can display confidential information that is provided by a patient or any other party supplying the information. As shown in FIG. 1, the first display 105 can display only a patient's name; however, the invention is not limited in this regard as the first display can also display other confidential information that can be concealed.

The first display 105 can be configured to conceal at least a portion of the confidential information in a variety of different arrangements. In one arrangement, the first display 105 can be programmed to display confidential information for a specified time period. For instance, the first display 105 can display any information that is entered for only 5 seconds, 10 seconds, 15 seconds, 20 seconds, and so on. After the time period expires, the first display 105 can conceal the confidential information by removing the information from the first display 105. Additionally, the first display can display other text and/or graphics to conceal the confidential information.

In another arrangement, the confidential information can be concealed at the request of the user. In such an arrangement, the user of the first display 105 can indicate when the information is to be concealed, such as when the user has completely provided all pertinent information. For example, a user may enter all relevant information, review the information entered for accuracy, and then select to conceal the information.

In still another arrangement, the information can be concealed as the information is entered. Thus, when a patient's name is input, the first display 105 can display only a few characters in a nonsensical order or some other indicator that a name has been entered. In such an arrangement, information can be entered more than once and compared to previous entries to ensure accuracy. Additionally, concealing confidential information is not limited to the methods discussed as one skilled in the art will readily understand that there are a variety of arrangements for concealing information on a first display 105. Furthermore, the arrangements are not exclusive and can be combined to compliment each other or as redundant safety mechanisms.

The first display 105 also can be configured to limit legible viewing from different vantage points. For instance, the screen of the first display 105 can include suitable technology, such as a passive matrix liquid crystal display, that does not provide a wide viewing angle. A passive matrix display will adequately display confidential information to the person providing such information without allowing bystanders to legibly view the information displayed by the first display 105. Thus, the first display 105 can be configured to display confidential information to only a direct view. In such an embodiment, while the first display 105 may be readily viewable by multiple parties from multiple vantage points, the first display 105 will not legibly display confidential information to a party with a view point at distance from or to the side of the first display 105.

An input system 110 can also be provided for allowing a patient to provide relevant and necessary information. The input system 110 can be communicably coupled to the first display 105 and can include any suitable system for inputting confidential information. For example, the input system 110 can include a keyboard and a mouse, a number pad, and even an interface with navigation and selection buttons. The input system 110 can also include a card reader and scanner for accepting cards with magnetic strips and/or smart cards, an optical scanner for reading linear bar codes and data matrix bar codes, and a port for accepting memory structures, such as memory cards and memory sticks. An input system 110 that can accept and/or read such devices can lesson the amount of information, such as the patient's insurance provider, address, and so forth, that is typically entered by a user.

One skilled in the art, however, would appreciate that the input system 110 and the first display 105 can be combined into a single unit. The first display 105 can include touch screen technology for allowing the patient to enter information by touching the screen with a finger and/or a stylus. Additionally, the input system 110 and the first display 105 can be combined with a laptop computer that provides a user interface to collect confidential information. Similarly, the input system 110 and first display 115 can also include a tablet personal computer, a personal digital assistant, and any suitable portable device.

The second display 115 can display the information that is provided by the patient and/or presented at the first display 110. The second display 115 can display the same confidential information displayed at the first display. Nevertheless, as shown in FIG. 1, the invention is not limited in this regard as the second display can display other information, such insurance provider information, current medications, allergies, medical history, and other confidential information. As will be discussed in further detail below, such information can be supplied over the network 150.

Similar to the first display 105, the second display 115 can also include any device, such as a liquid crystal display, cathode ray tube, plasma screen, and the like, that is suitable for displaying text and/or graphics. In one arrangement, the second display 115 can also be located in a secure area. For instance, the second display 115 can be located within a room that is separated from the location of the first display 105 and only accessible by authorized personnel. Thus, in the secure area, only authorized personnel can have access to confidential information that is viewable on the second display 115. Although not shown, the system 100 can include more than one display having attributes of the second display 115 so that such displays can be distributed throughout multiple locations of a facility.

In another arrangement, the second display 115 can be located proximate to the location of the first display 105, such as a nurses' station within a typical hospital emergency room. In such an arrangement, the second display 115 can include a suitable securing mechanism, such as software that allows access only after an identification and/or a password is provided. Additionally, the securing mechanism can include a card scanner and reader, a biometric identifier, such as a finger print scanner and/or a retinal scanner, and any other suitable mechanism for restricting access to only authorized personnel.

The system 100 can also include a housing 140 for arranging the first display 105 so that the confidential information is viewable by only the party providing the confidential information. For instance, the first display 105 can be disposed within a housing 140 that prevents unauthorized viewing by simply physically restricting the field of view to only the party providing information. Additionally, the housing 140 can provide a structure for supporting the first display 105. The input system 110 can also be supported by the housing 140. Thus, the first display 105, the input system 110, and the housing 140 can form a structure, such as a kiosk, that is accessible by a patient. The second display 115 can be arranged in a housing 145, similar to that of housing 140, to prevent unauthorized viewing and can be configured to limit legible viewing vantage perspectives.

The data store 125 can include any suitable medium for storing patient information as data. The data store 125 can include a hard drive, flash memory, random access memory ("RAM"), read only memory ("ROM"), and the like, for storing the patient information. Additionally, the data store can include multiple, separate data stores for mirroring stored data for retrieval and loss prevention.

The server 120 can include any suitable computing device that can generally interconnect the components of system 100 across the network 150. The server 120 can be programmed with suitable software and logic circuitry for interfacing with the various components of the system 100 and for analyzing and processing confidential information. The server 120 can fulfill requests by and provide services to the first display 105, input system 110, the second display 115, and the data store 125. Additionally, the server 120 can be an application server for providing applications to the first display 105, input system 110, the second display 115, and the data store 125. The server 120 can also be communicably coupled to a wireless transceiver 130, configured to communicate over any standard radio frequency such as cellular and Wi-Fi, for wireless communication with other devices, components, systems, and networks, that are within and outside of system 100.

In operation, a patient, or a user, can access a first display 105 and provide confidential information with the input system 110. The first display 105 can display the confidential information to allow the patient to review the information for completeness and/or accuracy. The first display 105 will display the confidential information for a predetermined amount of time or until the user requests that the information be concealed. In another arrangement, where no user request is received after a predetermined amount of time, the system 100 can automatically remove confidential information.

The confidential information can be transferred over the network 150 to the server 120 for processing, the data store 125 for storage, and the second display 115 for presentation to authorized personnel. Thus, at least a portion of the confidential information can be displayed on the second display 115 in real-time, or sometime thereafter. While processing the confidential information, the server 120 can correlate the confidential information received from the patient with other patient information available from the network 150, such as insurance information and/or medical records stored in the data store 125. Thus, with only the patient name provided, the server 120 can correlate the patient's name to the relevant stored data, and the server 120 can provide the relevant patient information to the second display 115 and/or appropriate party without requiring the patient to provide all such information. Further, with medical records and insurance information attainable with only the patient's name, the medical personnel can focus on providing medical care, instead of searching for patient information.

Furthermore, the server 120 can process the confidential information and dictate the portions of the confidential information that are presented at the second display 115. The server 120 can also dictate the format for storing the confidential information in the data store 125. At least a portion of the information stored in the data store 125 can be time-stamped to create a time and/or date based log of all the users generally accessing and using the system 100 and/or specifically accessing the first display 105.

In addition to displaying, concealing, and storing confidential information, at least a portion of the confidential information can be transmitted to an appropriate party, such as a doctor, nurse, physician's assistant, and the like. The information is preferably transferred via the server 120 and, in one arrangement, the server 120 can be configured to execute an application for managing patient data and/or patient scheduling. In this arrangement, the application executed by the server 120 can assign the patient to a particular health care professional and can provide patient medical records to the health care professional. Such information can be transmitted in any suitable manner, for example using a suitable modem that is communicatively linked to a communications network, as an electronic mail, an instant message, a text message, and/or the like. The transmission can include portions of the confidential information and/or can include a simple notification that a patient is present. The transmission can be sent locally, i.e. within an office, and can also be sent to a remote location over the Internet, a cellular communications link, public switched telephone network, and the like.

The invention is not limited in this regard, however, as the first display 105, input system 110, server 120, and the second display 115 can each be configured to transmit the information. For example, each display can be incorporated as part of a stand alone computer system connected to each other and/or the server 120 over the network 150, where each computer system executes suitable operational software for performing the actions and operations described herein. In an arrangement where the first display 105, the input system 110, the server 120, data store 125, and the second display 115 are in wireless communication, the information can be transmitted wirelessly to a cell phone, a beeper, a personal digital assistant, and the like. In such an arrangement, each of the first display 105 and/or the input system 110, the second display 115, and the data store 125 can include wireless transceivers (not shown).

Thus, when a patient enters confidential information, at least a portion of the information can be transmitted to the appropriate party as determined by the server 120. For instance, a doctor can receive a text message containing relevant confidential information, such as name, age, and reason for visit. Alternatively, a doctor can simply receive a notification that a patient has arrived. Further, notification, without any confidential information, can be sent to personnel that do not have or need access to the confidential information. For example, notification can be sent to a hospital worker to provide a wheelchair for the patient, to escort a patient to particular room, or to supply a room with specific supplies that will be needed by the patient.

Further, it should also be noted that the first display 105, the input system 110, and the second display 115 can be combined into one device. For instance, a handheld computer with a touch screen can be used as a first display 105, the input system 110, and the second display 115. In use, a user would enter confidential information into the handheld computer, the information can be concealed, and then the user can give the handheld computer to the appropriate party. Upon verifying the rights of an authorized user to access information via the entry of a suitable password or the like, the handheld computer can display the appropriate information to the accessing party. Additionally, the confidential information can be transmitted to the server 120 for processing and to the data store 125 for storage. Thus, in such an embodiment, only a portion of the information can be displayed allowing multiple parties to have multiple levels of access.

Figure 2:
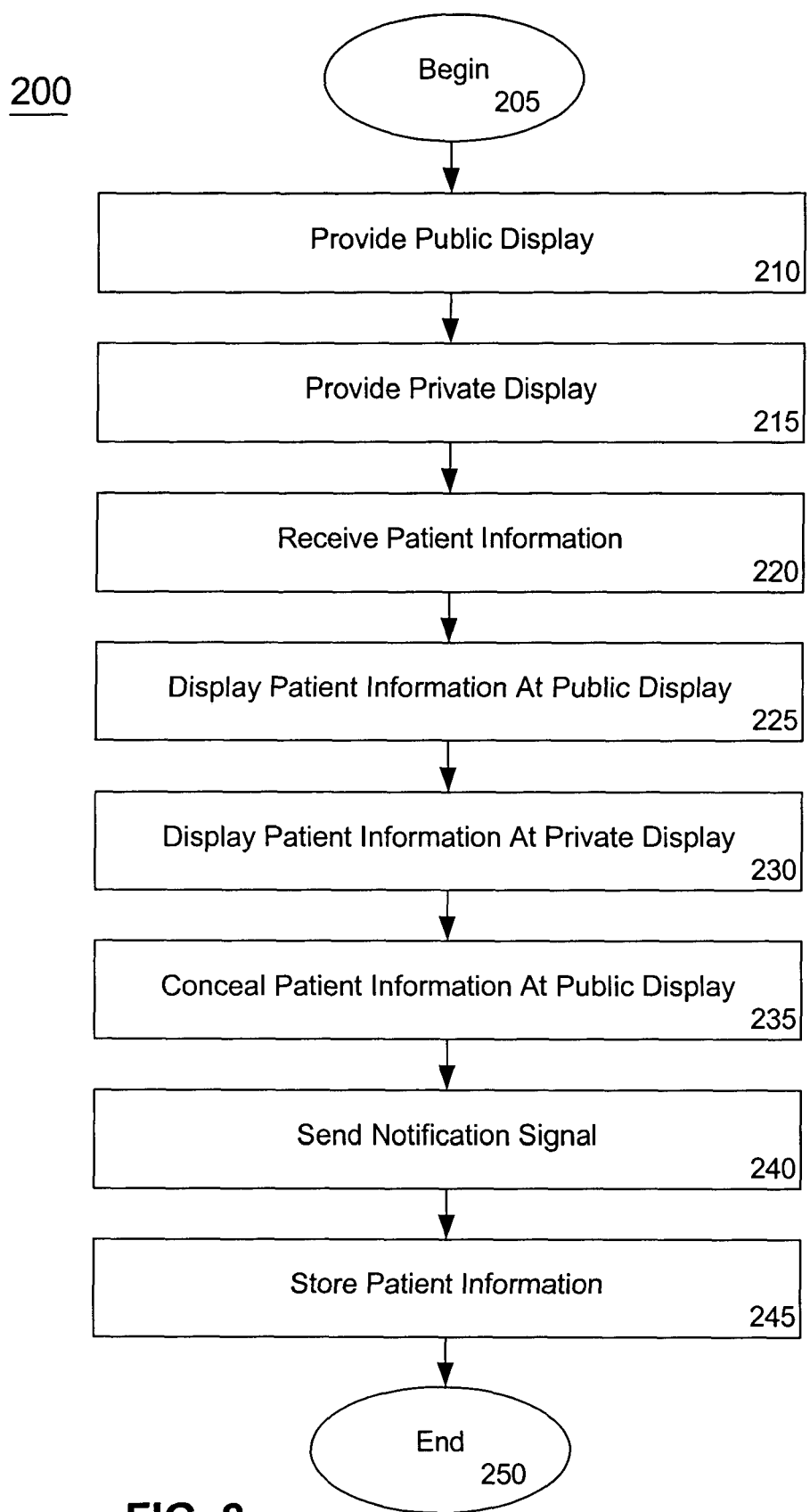
FIG. 2 is a flow chart illustrating a method for concealing displayed confidential information in accordance with the inventive arrangements.

A method for concealing displayed confidential information is also provided in accordance with the inventive arrangements. FIG. 2 is an exemplary flow chart that is helpful in understanding method 200. Method 200 can begin at step 205. In step 210, one or more publically accessible displays can be provided that can display information that is supplied by a user, such as patient supplied identifying and medical information. For instance, providing a publically accessible display can include providing a free standing kiosk that can display and conceal confidential information. Providing a publically accessible display can also include providing a patient with a handheld device, such as a tablet personal computer, that can display and conceal confidential information. The publically accessible display can include any device, such as a liquid crystal display, cathode ray tube, plasma screen, and the like, that is suitable for displaying text and/or graphics. Further, the publically accessible display can also include a personal computer, a laptop computer, a tablet computer, a personal computing device, and the like. Thus, the publically accessible display can collect information as well as display information.

The publically accessible display can be provided in any environment where a user typically provides confidential information. A non-exhaustive list of such environments can include a hospital emergency room, an outpatient center, a doctor office, a dentist office, and the like. Nevertheless, the method 200 is not limited to the type of environment in which it can be practiced as the method 200 can be practiced in any environment in which there is a desire to control access to displayed information.

Further, one or more publically accessible displays can be provided to allow multiple users to provide confidential information. For example, in a typical hospital emergency room environment, a multitude of patients may need to provide confidential information regarding their medical history. Providing one or more publically accessible displays, such as multiple handheld computers, can allow each patient to provide their relevant information simultaneously while keeping such information confidential.

In step 215, a private display can be provided that can display the information that is displayed by the publically accessible display. Providing a private display can include placing a private display, such as computing terminal, in a secure area that only authorized personal can access. The private display can be similar to the publically accessible display; however, access to the private display can be limited to authorized personnel. Access for authorized personnel can be controlled by placing the private display at a remote location and/or a secure location where all personnel are authorized to view the information displayed. For example, such a secure location can include a room that is separate from the first display. In alternative to, or in addition to providing the private display in a particular location, authorized access can be controlled via a security system, such as a login screen with a password, identification cards, identifying symbols, and the like. With such a security system, the private display can be provided in an unsecured area, such as a hospital waiting room.

In step 220, confidential information can be received. For example, receiving confidential information can include receiving a patient's name and/or social security number as the patient enters the information. In operation, confidential information that is provided by user is received, typically by the publically accessible display. For example, the publically accessible display can be a handheld computer with an input device, such as a keyboard or stylus used with a touch screen. The hand held computer can receive the information as input by the user. Additionally, it should be noted that the information being received can be provided by the patient, a doctor, a nurse, an insurance agency, and a database having stored confidential information. For instance, after a portion of the confidential information is received, other information, such a insurance provider information, can be correlated with the received information. Once correlated, all of the confidential information can be received.

In step 225, confidential information can be displayed at the publically accessible display. Displaying confidential information can include displaying all of the confidential information and can also include displaying only portions of the confidential information. For instance, displaying confidential information can include displaying the patient's name, social security number, reason for visit, medical records, and the like. The confidential information can be displayed to allow the patient to review the information. The information can be displayed as provided, i.e. in real-time, and can also be displayed when all information has been provided. Displaying confidential information allows the patient to review the information and check for accuracy.

In step 230, confidential information can be displayed at the private display. The information displayed can include information received from the patient, such as the patient's name and/or reason for visit, and can also include information received from another source, such as insurance provider information received from an insurance provider over the Internet. Displaying information at the private display provides the care provider with all the information necessary for providing appropriate medical care, billing questions, and relevant medical history. Displaying information at the private display can be concurrent with the display of confidential information at the publically accessible display; however, the invention is not limited in this regard as the confidential information can be displayed at the private display both before and after the information is displayed at the publically accessible display. While one possible configuration can display information at the publically accessible display and the private display in a similar or analogous format, the invention is not so limited as displaying information at the public and private displays can be presented in different formats. Further, the private display can display more or less information relative to the amount of information displayed at the publically accessible display. Similarly, if more than one private display is provided in step 215, each private display can display more or less information relative to the other private displays.

In step 235, confidential information can be concealed. Concealing information can include removing the information, covering the information, presenting the information in a nonsensical format, and the like. Concealing confidential information prevents people from viewing the information and can be accomplished in a variety of different arrangements. While some arrangements for concealing displayed information can be dependent upon the type of display, other arrangements are independent of the type of display. For instance, with a cathode ray tube or plasma monitor, the information can be concealed by simply displaying blank portions where the information was once displayed. Alternatively, the information can be concealed by changing the display from the information to a non-related picture and/or dynamic graphics. Further, the information can be concealed by physically blocking the display from view.

The step of concealing confidential information can be triggered by the occurrence of a multitude of events that can operate independently or in combination with each other. In one arrangement, confidential information can be concealed after the expiration of a predetermined time period. In such an arrangement, the confidential information can be concealed after the expiration of a predetermined time period that can start at the moment a portion of information is displayed. Also in such an arrangement, the confidential information can be concealed after the expiration of a predetermined time period that can start when all the confidential information has been displayed, which can allow the patient to review the information for completeness and accuracy.

In another arrangement, confidential information can be concealed based on a user request. Thus, instead of concealing the confidential information based on some period of time, the confidential information can be concealed immediately upon a request signal, such as a user selecting "CONCEAL" or "DONE" on the publically accessible display. Typically, a user can provide the request signal when all relevant information has been displayed; however, the invention is not limited in this regard as the information can be concealed even if all relevant information has not yet been displayed.

At step 240, a notification signal can be sent. The notification signal can be sent via any standard communication protocol, such as via a text message, an electronic mail, a cellular phone call, and the like. The notification signal can contain a portion of the displayed confidential information; however, the invention is not limited in this regard as the notification signal can provide only notification that a patient is present. Further, the notification can include other stored information, such as patient medical records, that were not displayed. In the preferred embodiment, the notification signal can be sent to a health care professional. Nevertheless, the notification signal can be sent to a multitude of other parties, including a hospital assistant that can escort a patient to the appropriate room, a nurse, a secretary, a physician assistant, a relative, and any other appropriate party.

In step 245, confidential information can be stored in the format in which the information is received or in some other format established after the information is processed. Stored confidential information can be used for future occasions to automate the supplying of confidential information. Alternatively, storing confidential information can include storing a log noting the date and time that confidential information was displayed. Such storing provides a time and/or date based log that indicates the volume and frequency of information displayed but does not provide the actual information displayed. Of course one skilled in the art will recognize that storing at least portions of confidential information can be combined with storing a time and date based log to produce a detailed log of confidential information that can be organized by time or date displayed. The information can be stored in any suitable data storage, such as a hard drive, a server, ROM, RAM, flash based memory, and the like.

Method 200 can end at step 250 or can continue with the repetition of any previous step. Additionally, it should be noted that steps of method 200 can be completed in other sequences than the sequence presented. Further, some steps of method 200 can be skipped and/or combined with other steps of method 200. For instance, step 210 of providing a publically accessible display and step 215 of providing a private display can be combined when one display, such as a hand held computer, can be used as both the publically accessible display and the private display.

To illustrate one example of method 200 in operation, a brief example is provided in the general environment of a hospital emergency room. Nevertheless, it should be noted that the example is merely one example of the many different circumstances in which method 200 can be practiced. Thus, the method 200 is not limited to the circumstances below.

A patient can walk into an emergency room where a publically accessible display is provided (step 210) in the waiting room and a private display is provided (step 215) behind a nurse's station. The patient can enter confidential information, such as name, social security number, and reason for medical visit, to the input system and publically accessible display which receive (step 220) the patient information. The publically accessible display can also receive (step 220) patient information from a network having databases of insurance information, medical history, and the like. Once the publically accessible display has received the information, the publically accessible display can display (step 225) the information to the patient.

The patient information can also be displayed at the private display (step 230) for review by a nurse. With the patient information displayed, the nurse can provide the proper emergency care and coordinate an appointment for the patient with the appropriate doctor to treat the reason for the patient's arrival at the emergency room. In the meantime, or even before the display of patient information at the private display, the patient information on the publically accessible display can be concealed (step 235) at the user's request by the user selecting a "CONCEAL" or "DONE" button on the publically accessible display. Nevertheless, the pubic display can be configured with a fail safe mechanism that will automatically conceal the patient information after the expiration of a predetermined time period even if the user fails to select the "CONCEAL" button.

Contemporaneously, a notification signal can be sent (step 240) to a doctor. In this example, the notification signal can include a portion of the patient information received from the patient and a portion of the patient information received from the network. Thus, the doctor is provided with the necessary information, such as the patient's name, reason for visit, and medical history, to properly treat the patient. Additionally, the patient information can be stored (step 245) to keep a log of the patients admitted, treated, and/or diagnosed at the emergency room. The patient can now receive the appropriate medical treatment without having any unauthorized disclosures of patient confidential information (i.e., the method can end at step 250).

The present invention can be realized in hardware, software, or a combination of hardware and software. The present invention can be realized in a centralized fashion in one computer system or in a distributed fashion where different elements are spread across several interconnected computer systems. Any kind of computer system or other apparatus adapted for carrying out the methods described herein is suited. A typical combination of hardware and software can be a general-purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention can be embodied in other forms without departing from the spirit or essential attributes thereof. Accordingly, reference should be made to the following claims, rather than to the foregoing specification, as indicating the scope of the invention.

What is claimed is:

1. A method for concealing displayed confidential patient information comprising the steps of:
   providing a system including at least one publically accessible display for displaying confidential information of a patient and at least one private display for displaying the confidential information displayed by the publically accessible display, wherein the private display is accessible only to authorized health care personnel, wherein the at least one publically accessible display and at least one private display are connected through a network;
   receiving patient identification information supplied by the patient from an input device connected to the publically accessible display;
   retrieving patient information from a central data store based on the supplied patient identification information;
   displaying the confidential information including the supplied patient identification information and the retrieved patient information at the publically accessible display for a predetermined time period, wherein the publically accessible display is disposed within a housing so that the confidential information is only viewable by the patient;
   displaying the confidential information at the private display for review by the authorized health care personnel;
   concealing the confidential information displayed at the publically accessible display upon expiration of the predetermined time period or upon a request of the patient, the concealing step including at least one of:
      removing the confidential information from the publically accessible display;
      covering the confidential information; and
      presenting the information in a nonsensical format;
   sending a notification signal to the authorized health care personnel indicating that the patient is present; and
   storing at least a portion of the confidential information in a local data store for the patient to receive proper treatment.

2. A system for concealing displayed confidential patient information comprising:
   at least one publically accessible display for displaying confidential information of a patient, the publically accessible display being disposed within a housing so that the confidential information is only viewable by the patient;
   an input device for receiving the patient identification information supplied by the patient, the input device being connected to the publically accessible display;
   a central data store from which patient information can be retrieved based on the supplied patient identification information;
   at least one private display for displaying the confidential information displayed by the publically accessible display, wherein the private display is accessible only to authorized health care personnel, wherein the at least one publically accessible display and at least one private display are connected through a network;
   a device for sending a notification signal to the authorized health care personnel indicating that the patient is present; and
   a local data store for storing at least a portion of the confidential information for the patient to receive proper treatment;
   wherein the confidential information including the supplied patient identification information and the retrieved patient information is displayed at the publically accessible display for a predetermined time period;
   wherein the confidential information displayed at the publically accessible display is concealed upon expiration of the predetermined time period or upon a request of the patient;
   wherein the confidential information is concealed by at least one of removing the confidential information from the publically accessible display, covering the confidential information, and presenting the information in a nonsensical format.

3. The system according to claim 2, further comprising at least one wireless transceiver for at least one of sending and receiving at least a portion of the confidential information.

4. A machine readable storage, having stored thereon a computer program having a plurality of code sections executable by a machine for causing the machine to perform the steps of:

providing a system including at least one publically accessible display for displaying confidential information of a patient and at least one private display for displaying the confidential information displayed by the publically accessible display, wherein the private display is accessible only to authorized health care personnel, wherein the at least one publically accessible display and at least one private display are connected through a network;

receiving patient identification information supplied by the patient from an input device connected to the publically accessible display;

retrieving patient information from a central data store based on the supplied patient identification information;

displaying the confidential information including the supplied patient identification information and the retrieved patient information at the publically accessible display for a predetermined time period, wherein the publically accessible display is disposed within a housing so that the confidential information is only viewable by the patient;

displaying the confidential information at the private display for review by the authorized health care personnel;

concealing the confidential information displayed at the publically accessible display upon expiration of the predetermined time period or upon a request of the patient, the concealing step including at least one of:
     removing the confidential information from the publically accessible display;
     covering the confidential information; and
     presenting the information in a nonsensical format;

sending a notification signal to the authorized health care personnel indicating that the patient is present; and storing at least a portion of the confidential information for the patient to receive proper treatment.

* * * * *